United States Patent [19]

Kraus et al.

[11] Patent Number: 5,704,919
[45] Date of Patent: Jan. 6, 1998

[54] INTRAVENOUS CANNULA ASSEMBLY

[75] Inventors: Menahem Kraus, Rehovot; Eli Shemesh, Ashdod; Eitan Rogel, Haifa, all of Israel

[73] Assignee: Travenol Laboratories (Israel) Ltd., Ashdod, Israel

[21] Appl. No.: 446,813

[22] PCT Filed: Dec. 3, 1993

[86] PCT No.: PCT/US93/11719

§ 371 Date: Sep. 5, 1995

§ 102(e) Date: Sep. 5, 1995

[87] PCT Pub. No.: WO94/13341

PCT Pub. Date: Jun. 23, 1994

[30] Foreign Application Priority Data

Dec. 4, 1992 [IL] Israel ......... 103973

[51] Int. Cl.⁶ .......... A61M 5/00
[52] U.S. Cl. .......... 604/192; 604/198; 604/167
[58] Field of Search .......... 604/110, 164, 604/192, 198, 167, 264, 280

[56] References Cited

U.S. PATENT DOCUMENTS

| | | |
|---|---|---|
| 3,774,604 | 11/1973 | Danielsson . |
| 3,895,632 | 7/1975 | Plowiecki . |
| 3,977,400 | 8/1976 | Moorehead . |
| 4,000,739 | 1/1977 | Stevens . |
| 4,126,133 | 11/1978 | Schwartz . |
| 4,245,635 | 1/1981 | Kontos . |
| 4,540,411 | 9/1985 | Bodicky . |
| 4,580,573 | 4/1986 | Quinn . |
| 4,762,516 | 8/1988 | Luther et al. . |
| 4,775,369 | 10/1988 | Schwartz . |
| 4,834,718 | 5/1989 | McDonald ............... 604/195 |
| 4,850,994 | 7/1989 | Zerbst et al. . |
| 4,867,172 | 9/1989 | Haber . |
| 4,897,083 | 1/1990 | Martell . |
| 4,934,718 | 6/1990 | McDonald . |
| 4,935,013 | 6/1990 | Haber ............... 604/192 |
| 4,944,728 | 7/1990 | Carrell et al. . |
| 4,950,250 | 8/1990 | Haber et al. . |
| 4,950,260 | 8/1990 | Bonaldo . |
| 4,955,866 | 9/1990 | Corey . |
| 4,986,817 | 1/1991 | Code . |
| 4,986,819 | 1/1991 | Sobel . |
| 4,994,034 | 2/1991 | Botich et al. . |
| 5,019,049 | 5/1991 | Haining . |
| 5,024,616 | 6/1991 | Ogle . |
| 5,051,109 | 9/1991 | Simon . |
| 5,098,394 | 3/1992 | Luther . |
| 5,098,405 | 3/1992 | Peterson et al. . |
| 5,102,394 | 4/1992 | Lasaitis et al. . |
| 5,120,320 | 6/1992 | Fayngold . |
| 5,131,405 | 7/1992 | Burns . |
| 5,167,635 | 12/1992 | Haber et al. . |
| 5,328,482 | 7/1994 | Sircom et al. . |
| 5,334,161 | 8/1994 | Gurmarnik . |

FOREIGN PATENT DOCUMENTS

93/08865  5/1993  WIPO .

*Primary Examiner*—Sam Rimell
*Attorney, Agent, or Firm*—Ladas & Parry

[57] ABSTRACT

An intravenous cannula assembly having a cannula with a distal end insertable into a patient, a guide needle movable to an operative position with respect to the cannula and having as distal end for piercing the patient. The guide needle is movable to a retracted position via the proximal end of the cannula for removal therefrom and having a protective enclosure for enclosing the guide needle.

11 Claims, 6 Drawing Sheets

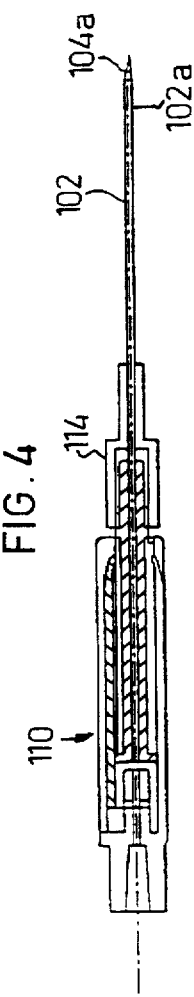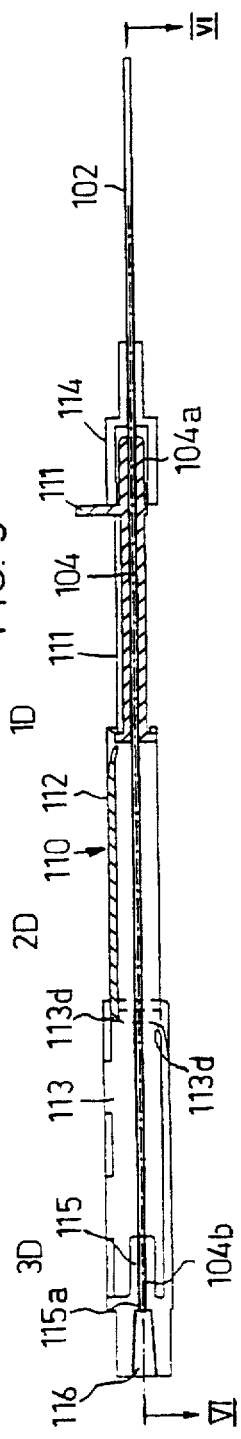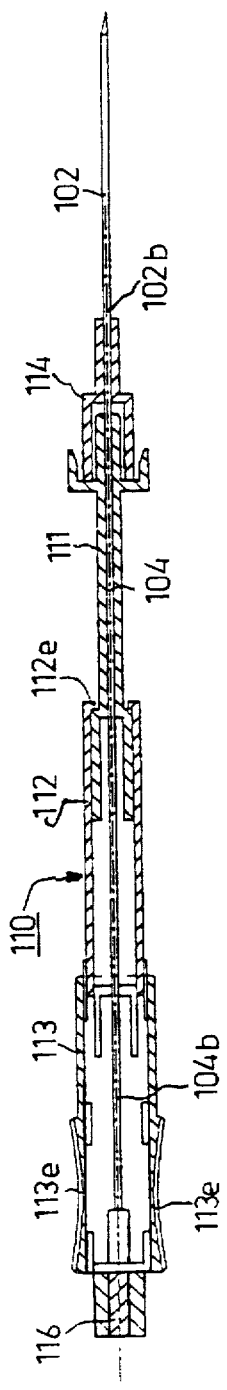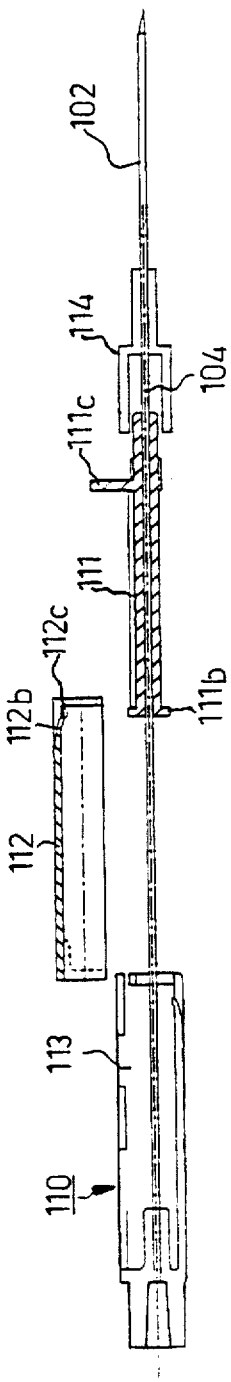

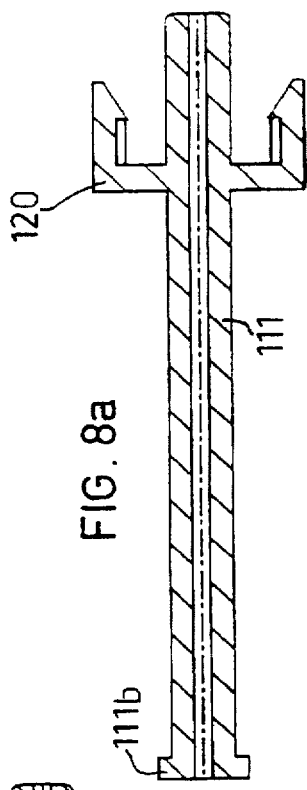
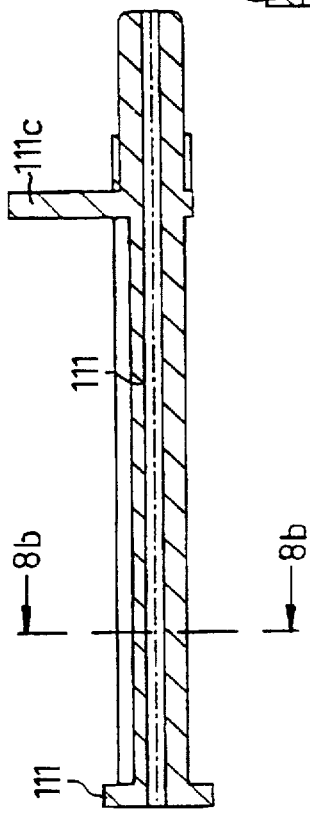
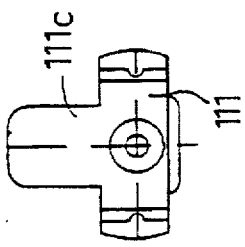
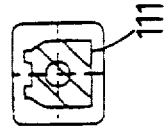
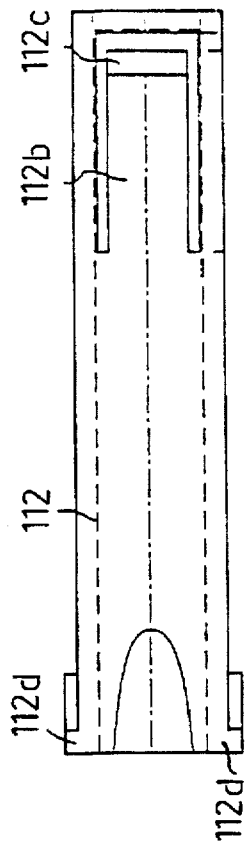
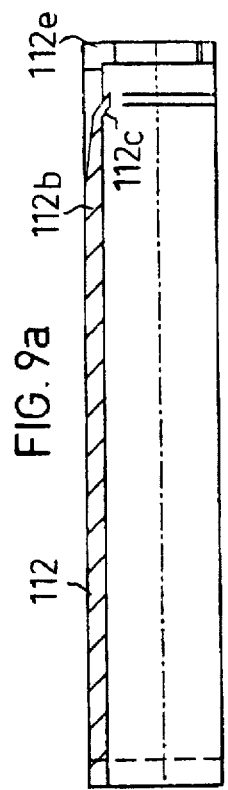
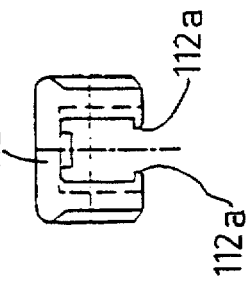

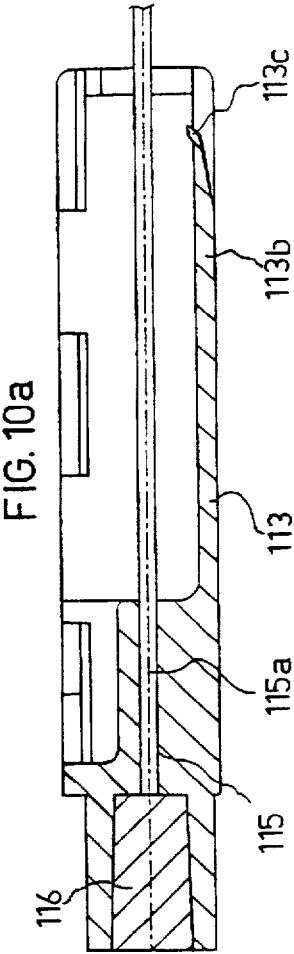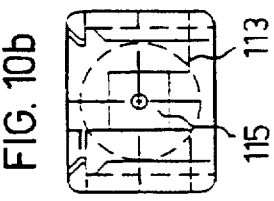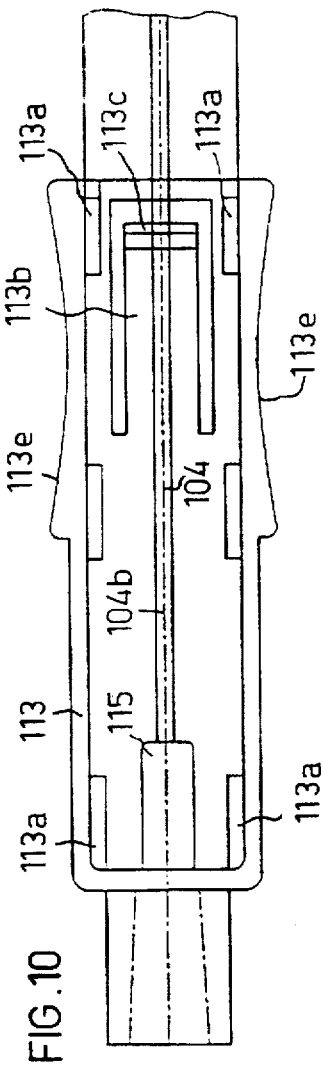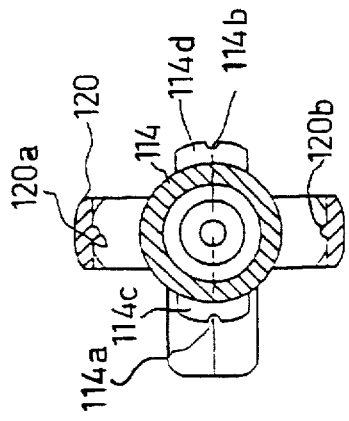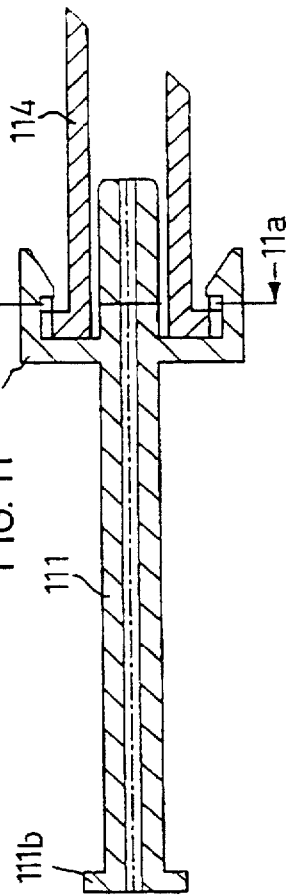

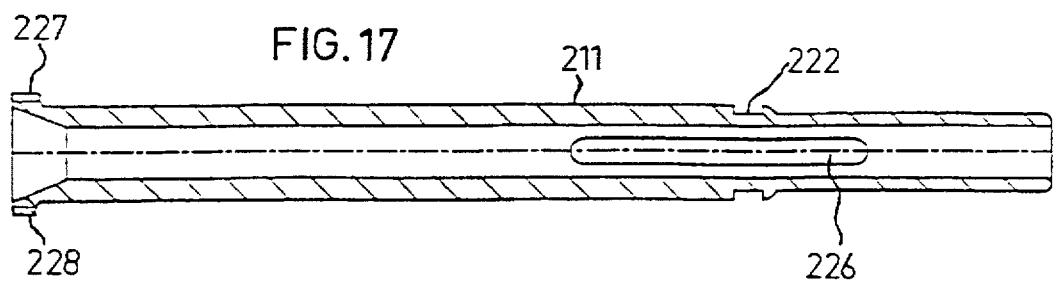
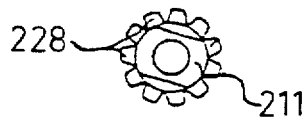
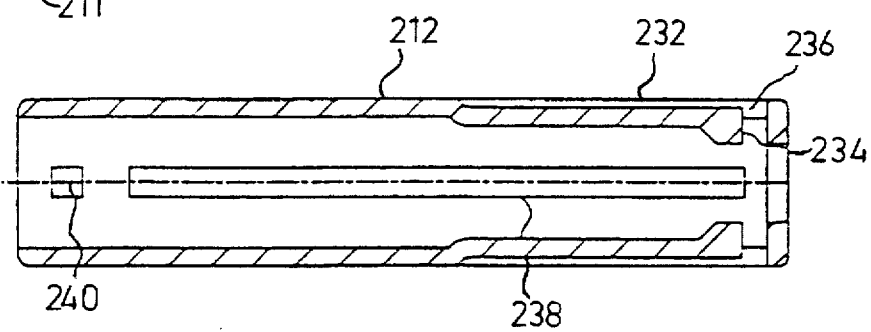
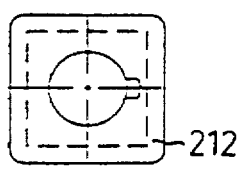
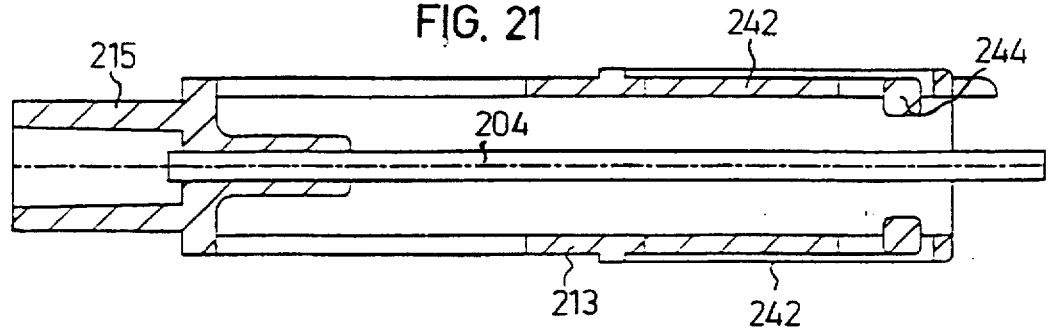
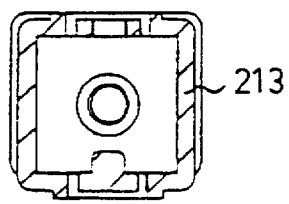
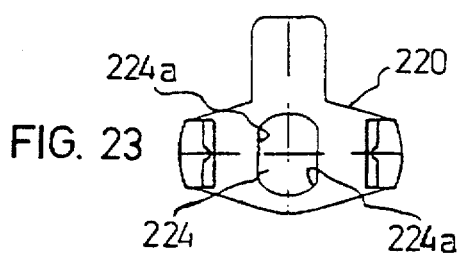

INTRAVENOUS CANNULA ASSEMBLY

TECHNICAL FIELD

The present invention relates to an intravenous cannula assembly, and particularly to an assembly which includes a cannula and a guide needle which is used for piercing the subject's skin and for guiding the cannula through the so-formed opening in the skin, after which the guide needle is withdrawn. The cannula so inserted into the subject's skin is then used for draining fluid or for introducing a medication. The invention is particularly directed to an intravenous cannula assembly which provides protection for healthcare personnel from inadvertent contact with the end of the guide needle after it has been contaminated by the subject's blood.

BACKGROUND ART

According to current practise, venous access for draining fluid or for introducing a medication is generally established as follows: A plastic cannula, e.g., of Teflon (Reg.™) or polyurethane, containing a hollow, metal guide-needle, is inserted into the subject's vein. Once blood flow through the needle is observed, the needle is withdrawn while holding the cannula inside the vein. The needle is then discarded while preventing blood outflow from the cannula, and a connection is made from the cannula to the intravenous set.

Once the needle has pierced the subject's skin, it becomes contaminated with the subject's blood, and therefore there is a danger of infecting healthcare personnel subsequently coming in contact with the needle. This danger is particularly real because of the many simultaneous operations involved in intravenous infusion and in emergency situations which may arise and which may prevent careful attention to the safety of the healthcare personnel. This danger can also be health-threatening because of the possibility of contracting AIDS in this manner.

Many types of protective devices have been developed to reduce the danger, but none of the devices which are now commercially available is entirely satisfactory. For example, some of the cannula assemblies developed for this purpose hamper or substantially change the common practise of establishing venous access for intravenous infusion. Others do not provide automatic protection, but rather necessitate a special needle protection step which may often be sidestepped. Still others require cannula assemblies which are substantially larger than the products used in the current practise.

For example, one commercially-available product includes a cover which covers the needle before it is inserted and which is subsequently removed and then used to protect the extracted needle. However, this product substantially changes the common procedure for establishing venous access, and moreover it is not automatic but rather requires the operator to take a special protection step, namely to reapply the cover to the extracted needle. In addition, the product is long and cumbersome.

U.S. Pat. No. 4,955,866 describes a protective cover tethered to a needle, the cover being applied to the needle tip after it has pierced the skin. However, this device also requires special attention of the user; moreover, it protects only the needle tip from contact and not the remainder of the needle which may also be contaminated.

Another product, described in U.S. Pat. No 4,832,696, includes a cylinder which receives the needle after its removal. However, this device is substantially larger than the current products, its length by necessity being more than twice the length of the needle, which makes it large and cumbersome to use.

U.S. Pat. No. 4,897,083 describes another device, in the form of a syringe, with a needle protected by a telescoping mechanism. However, in this device the mechanism must be manually contracted before use, and manually extended after use. Such a non-automatic operation is highly inefficient and undesirable.

An object of the present invention is to provide an intravenous cannula assembly having advantages in the above respects.

DISCLOSURE OF INVENTION

According to the present invention, there is provided an intravenous cannula assembly, comprising a cannula having a distal end insertable through an opening in a subject's skin for draining fluid or for introducing a medication via its proximal end; a guide needle in an operative position with respect to the cannula and having a distal end for piercing the subject's skin and for guiding the distal end of the cannula through the subject's skin, the guide needle being movable to a retracted position via the proximal end of the cannula; and a protective enclosure for enclosing the guide needle when moved to its retracted position. The protective enclosure comprises a plurality of sections in telescoping relation to each other including an inner section closed at its proximal end by a proximal end wall and open at its distal end, an intermediate section open at both ends, and an outer section open at both ends. The proximal end of the cannula has a hub secured to the distal end of the outer enclosure section by a quickly-attachable connector. The proximal end of the guide needle is secured to the proximal end wall of the inner enclosure section such that when the enclosure sections are in a compact nested condition, the guide needle is in its operative position extending through the inner, intermediate and outer enclosure sections and through the cannula, and when the enclosure sections are in an extended protective condition, the guide needle is completely enclosed by the inner, intermediate and outer enclosure sections.

According to further preferred features in the described embodiments, the quickly-attachable connector includes a pair of diametrically-opposed ribs fixed to the outer section of the protective enclosure, and a pair of diametrically-opposed ribs fixed to the cannula hub. One pair of ribs are formed with radially-extending projections receivable within recesses formed in the other pair of ribs, such that the protective enclosure, with the guide needle enclosed thereby, may be rotated in either direction to quickly detach it from the cannula.

Three embodiments of the invention are described below for purposes of example. In all three described embodiments, the protective enclosure includes blocking means carried by the plurality of sections of the protective enclosure permitting movement of the sections from the compact nested condition to the extended protective condition, but blocking movement of the sections from the extended protective condition to the compact nested condition. Also, in all three described embodiments, the protective enclosure is a three-section construction, including an intermediate section between its inner and outer sections.

As will be described more particularly below, an intravenous cannula assembly constructed in accordance with the foregoing features provides a number of important advantages over the known devices. Thus, it can be constructed so as not to be substantially larger than current products.

Moreover, it provides automatic protection when withdrawing the needle from the cannula and does not require a special needle protection step, as distinguished for example from the device described in U.S. Pat. No. 4,897,083 which requires manual contraction of the telescoping mechanism before use, and manual extension after use in order to provide the protection against contact with the needle. Further, the device prevents re-extraction of the needle from its contracted protected condition. In addition, it is simple to use and inexpensive to manufacture.

Further features and advantages of the invention will be apparent from the description below.

BRIEF DESCRIPTION OF DRAWINGS

The invention is herein described, by way of example only, with reference to the accompanying drawings, wherein:

FIGS. 4 and 5 are views, corresponding to those of FIGS. 1 and 2, respectively, illustrating a second form of intravenous cannula assembly constructed in accordance with the present invention;

FIG. 6 is a sectional view of FIG. 5 along line VI—VI;

FIG. 7 is a view similar to that of FIG. 5 but showing how the three sections of the protective enclosure are assembled;

FIGS. 8 and 8a–8c are enlarged views more particularly illustrating the construction of the outer section of the protective enclosure in FIGS. 4–7;

FIGS. 9, 9a and 9b are enlarged views more particularly illustrating the construction of the intermediate section of the protective enclosure in FIGS. 4–7;

FIGS. 10, 10a and 10b are enlarged views more particularly illustrating the construction of the inner section of the protective enclosure in FIGS. 4–7;

FIGS. 11, 11a and 11b more particularly illustrate the Leuer connection in the assembly of FIGS. 4–10;

FIG. 17 illustrates the outer section of the enclosure of FIGS. 12–15;

FIG. 18 is an end view thereof;

FIG. 19 illustrates the intermediate section of the enclosure of FIGS. 12–15;

FIG. 20 is an end view thereof;

FIG. 21 is a sectional view illustrating the inner section of the enclosure of FIGS. 12–15;

FIG. 22 is a transverse section thereof; and

FIG. 23 is an end view illustrating the Leuer coupling used in the cannula assembly of FIGS. 12–15.

MODES FOR CARRYING OUT THE INVENTION

Figure 1:
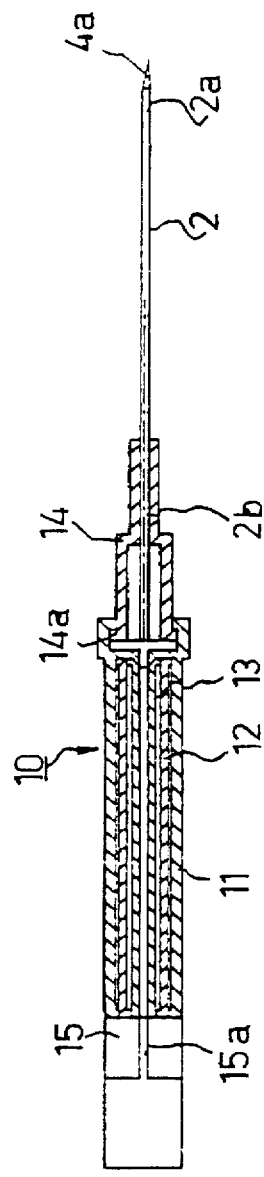
FIG. 1 is a longitudinal sectional view illustrating one form of intravenous cannula assembly constructed in accordance with the present invention, the assembly being shown with the guide needle in its operative position preparatory for use of the assembly.
Figure 2:
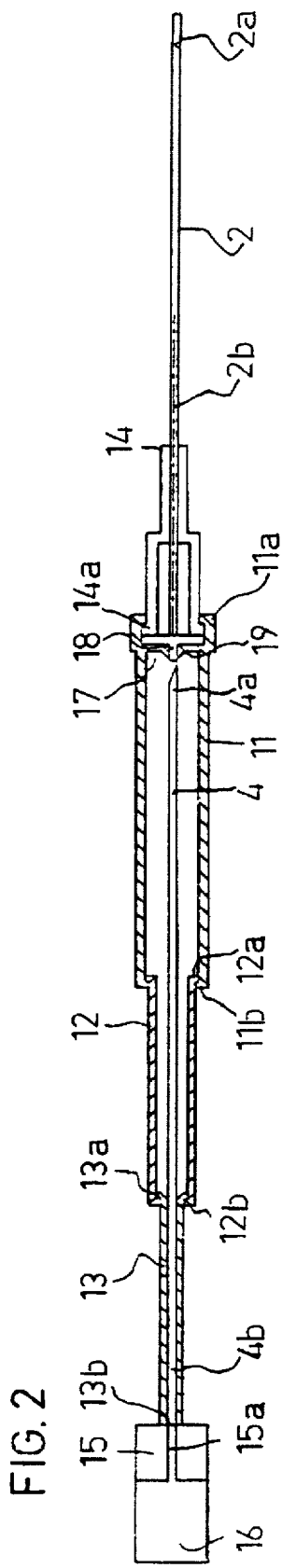
FIG. 2 is a view similar to that of FIG. 1 but showing the needle in its retracted position after use of the assembly.
Figure 3:
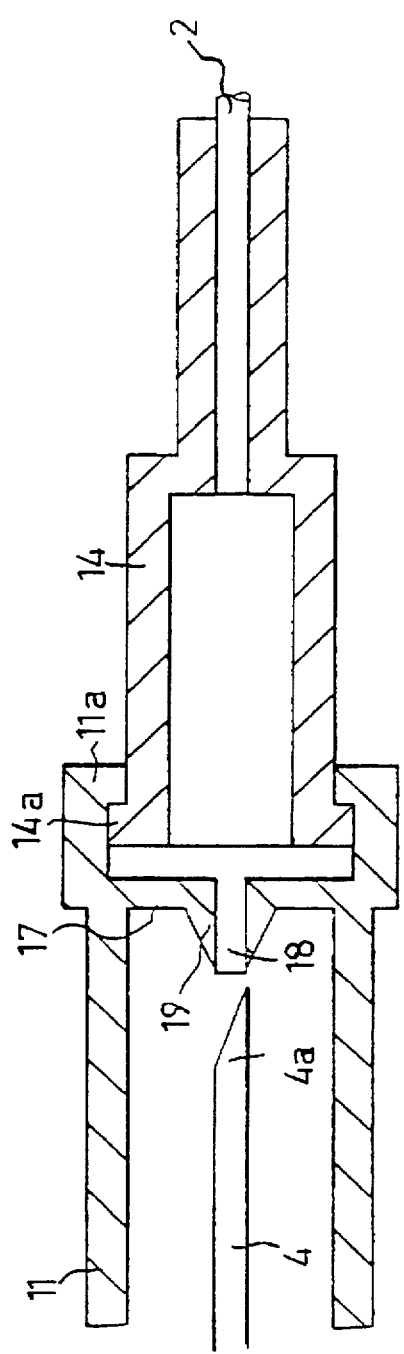
FIG. 3 is an enlarged fragmentary view of a portion of the assembly of FIG. 2.
Figure 12:
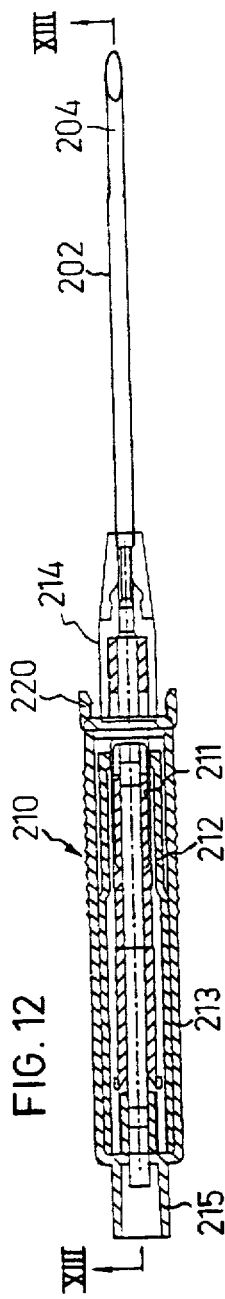
FIGS. 12 and 13 are sectional views illustrating a third form of cannula assembly constructed in accordance with the invention and illustrating the guide needle in its operative position, FIG. 13 being a sectional view along line XIII—XIII of FIG. 12.
Figure 13:
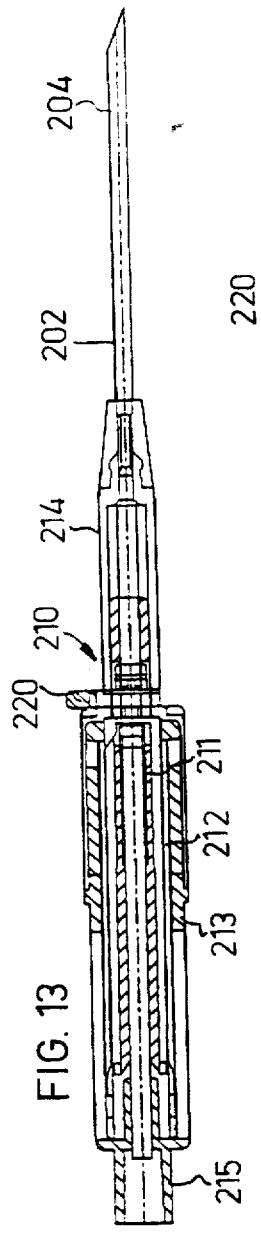

The intravenous cannula assembly illustrated in FIGS. 1–3 of the drawings is of the type which includes an outer plastic cannula 2 and an inner, hollow, metal guide-needle 4 movable within the cannula 2. In the operative position of the guide needle 4 illustrated in FIG. 1, its sharpened distal end 4a is used for piercing the subject's skin and for guiding the distal end 2a of the cannula into the opening so formed in the subject's skin. Once blood flow through the needle 4 is observed, the needle is moved to its retracted position through the proximal end 2b of the cannula 2, as shown in FIG. 2. The needle is then detached from the cannula and discarded, leaving the cannula 2 inside the vein. The cannula is then connected to the intravenous set for draining a fluid (e.g., blood) from the subject's body, or for introducing a medication into the subject's body.

Before the needle 4 is used for piercing the subject's skin, it is in a sterilized condition, and therefore there is no danger of contaminating healthcare pesonnel. However, once the needle has pierced the subject's skin, it becomes contaminated with the patient's blood, and therefore it must be protected from inadvertent needle sticks or other contact with healthcare personnel.

For the latter purpose, the assembly illustrated in the drawings includes a protective enclosure, generally designated 10, for enclosing the guide needle 4 when moved to its retracted position (FIG. 2). The protective enclosure 10 includes a plurality of sections, 11, 12 and 13. These sections are all of rectangular cross-section, decreasing in transverse dimensions from the inner section 11 to the outer section 13. That is, the transverse dimensions of the intermediate section 12 are smaller than those of the outer section 11, but larger than those of the inner section 13.

In the normal operative position of the guide needle 4 as illustrated in FIG. 1, sections 11–13 are in a contracted, nesting, telescoping relation to each other; however, in the retracted position of the needle, as illustrated in FIG. 2, these sections are extended to a total length to completely enclose the extracted needle, and thereby to prevent contact with it by healthcare personnel subsequently handling the extracted needle.

More particularly, the proximal end 2b of the cannula 2 is secured to one end of a cannula hub 14. The opposite end of the cannula hub is formed with an outturned annular rib 14a which detachably engages an inturned annular rib 11a of the outer telescoping section 11. The inner end of telescoping section 11 is similarly formed with an inturned annular rib 11b engageable with an outturned annular rib 12a formed in the outer end of the intermediate telescoping section 12. The inner end of telescoping section 12 is similarly formed with an inturned annular rib 12b engageable with an outturned rib 13a formed in the inner end of the inner telescoping section 13.

The proximal end of the hollow needle 4 is secured to a needle hub 15, which in turn is secured to the inner telescoping section 13 of the protective enclosure 10. The needle hub 15 is formed with a bore 15a aligned with the hollow interior of needle 4. This bore is closed by a plug 16, which is porous and hydrophobic enabling the venting of air and preventing blood from seeping out.

The outer end of the outer telescoping section 11 is closed by an end wall 17 formed with a center bore 18 having a diameter substantially equal to the outer diameter of the hollow needle 2. The outer surface of end wall 17 includes a conical protrusion 19 through which bore 17 is formed.

Protrusion 19 decreases in diameter in the inner direction, i.e., in the direction of the telescoping sections 12 and 13. This arrangement serves as a safety means permitting the guide needle 4 to move through bore 18 in one direction, from the operative position of the needle (FIG. 1) to its retracted position (FIG. 2), but not in the opposite direction, i.e., from its retracted position to its operative position.

The cannula assembly illustrated in FIGS. 1-3 of the drawings is used in the following manner:

The assembly is normally supplied in the condition illustrated in FIG. 1. In this normal condition of the assembly, the guide needle 4 is in its operative position with its distal end 4a projecting through the distal end 2a of the cannula 2, and the protective enclosure 10 is in its contracted condition, i.e., telescoping sections 12 and 13 both telescoped within section 11. The assembly would normally be packaged and sterilized in this condition as illustrated in FIG. 1.

When the assembly is to be used for drawing fluid (e.g., blood), or for administering a medication to a subject, the distal end 4a of the needle 4, together with the distal end 2a of the cannula 2, is inserted into the subject's vein. Successful insertion of the needle and cannula is noted by the flow of blood through the needle and the bore 15a in the needle hub 15. As soon as blood flow is observed, the inner telescoping section 13, together with the needle hub 15, is moved (leftwardly, FIG. 1) to extract the needle from the subject and also from the cannula 2. The inner telescoping section 13 is moved until its annular rib 13a engages annular rib 12b of the intermediate telescoping section 12, thereby causing that section to move until its annular rib 12a engages annular rib 11b of the outermost telescoping section 11.

During this expansion of the three telescoping sections 11, 12 and 13 of the protective enclosure 10, needle 4, being secured to the innermost telescoping section 13, is moved through the tight-fitting bore 18 out from the cannula 2 and its base 14, so that in the fully extended condition of the protective enclosure, the needle 12 is completely enclosed within the three telescoping sections 11-13, as shown in FIG. 2. The tight-fitting bore 18 formed in the end wall 17 of the outermost telescoping section 11, and the conical protrusion 19 through which bore 18 is formed, prevent the needle 4 from being moved in the reverse direction, i.e., back into the cannula 2.

When the needle 4 has thus been moved to its fully retracted position as illustrated in FIG. 2, wherein it is completely enclosed within the three telescoping sections 11-13 of the protective envelope 10, the protective envelope 10 is easily detached from the cannula hub 14 and discarded. The cannula hub may then be connected to a device for receiving fluid (e.g., blood) drained from the subject, or to a device for supplying fluid (e.g., medication) to be introduced into the subject via the cannula 2.

The intravenous cannula assembly illustrated in FIGS. 4–10 is of a similar type as that of FIGS. 1–3. It includes an outer plastic cannula 102, an outer hollow metal guide needle 104, and a protective enclosure 110 for enclosing the guide needle when moved to its retracted position, as described above with respect to FIGS. 1–3. The protective enclosure 110 also includes a plurality of telescoping sections 111, 112 and 113, also of rectangular cross-section, but in this case the transverse dimensions of the sections increase from the outer section 111 to the inner section 113; that is, the transverse dimensions of the intermediate section 112 are larger than those of the outer section 111 and smaller than those of the inner section 113, which is opposite to the arrangement in FIGS. 1–3.

The intermediate section 112 is open at one side, as shown particularly in FIGS. 9a and 9b, and is formed with a pair of inwardly-directed ribs 112a adapted to be snapped over the outer face of the outer section 111, and also over outwardly-projecting ribs 113a on the outer face of the inner section 113, in order to assemble the three sections together. The upper wall of the intermediate section 112 is further formed with a resilient tongue 112b which, when the intermediate section is moved with respect to the outer section 111, rides over an annular rib 111b formed at the proximal end of the outer section 111. The tip 112c of tongue 112b is bent inwardly such that when the intermediate section 112 has been moved to its outermost position with respect to the outer section 111, tongue 112b moves inwardly, under its inherent resiliency, to cause its tip 112c to engage the outer face of rib 111b, and thereby to prevent the intermediate section 112 from moving in the reverse direction (i.e., to its nested condition) with respect to the outer section 110.

The inner section 113 (FIG. 10) of the protective enclosure 110 is also open at one side and is similarly formed with a resilient tongue 113b terminating in an inwardly-bent tip 113c. This tip also permits the inner section to move outwardly with respect to the intermediate section 112, and engages ribs 112d at the end of the intermediate section to prevent the inner section from moving in the opposite direction (towards its nested condition) with respect to the intermediate section 112.

The proximal end 102b of the cannula 102 is also secured to one end of a cannula hub 114, as in FIGS. 1–3. In this case, however, the opposite end of the cannula hub 114 is secured to the distal end of the outer protective enclosure section 111 by means of a Leuer connection 120 (FIG. 11), which includes a pair of projections 120a, 120b receivable in recesses 114a, 114b formed in a pair of ears 114c, 114d fixed to the cannula hub 114. This Leuer connection permits the protective enclosure to be conveniently attached to or detached from the cannula hub by merely rotating one with respect to the other, as shown in FIG. 11a (attached condition) and FIG. 11b (detached condition).

The proximal end of the hollow needle 104 is secured to a needle hub 115 (FIG. 10) fixed to the inner telescoping section 113 of the protective enclosure 110, similar to the arrangement of FIGS. 1–3. The inner face of the outer section 113 is dished at its opposite sides, as shown at 113e, to permit convenient gripping of that section between the user's thumb and second finger, while the user's index finger engages an upstanding post 111c (FIGS. 7, 8) formed in the distal end of the outer section 111. Bore 115a formed through the needle hub 115 is normally closed by hydropohobic plug 116, corresponding to plug 16 in FIGS. 1–3.

The distal end of the inner section 113 is further formed with a pair of stops 113d which are engageable with a pair of shoulders 112d formed at the proximal end of the intermediate section 112, to limit the outermost position of the inner section 113 with respect to the outer section 112. Similarly, the distal end of the intermediate section 112 is formed with an inwardly-directed shoulder 112e, engageable with an outer rib 111b formed at the proximal end of the outer section 111, to limit the outermost position of the intermediate section with respect to the outer section.

The cannula assembly illustrated in FIGS. 4–11 is used in the following manner.

The assembly is normally supplied in the compacted condition illustrated in FIG. 4, wherein the guide needle 104 is in its operative position with its end 104a projecting through the end 102a of the cannula 102, and the protective enclosure 110 in its contracted, nested condition. The assembly would normally be packaged and sterilized in this condition.

When the assembly is to be used, the distal end 104a of the needle 104, together with the distal end 102a of the cannula 102, is inserted into the subject's vein. This is conveniently facilitated by gripping the dished surfaces 113e of the inner section 113 between the user's thumb and second finger, while the user's index finger engages the upstanding post 111c.

As soon as blood flow is observed, the inner telescoping section 113, together with its needle hub 115, is moved to extract the needle from the subject and also from the cannula 102. First, the inner section 113 moves with respect to the intermediate section 112, until tongue 113b snaps its tip 113c into engagement with the end of the intermediate section 112; and then the intermediate section 112 moves with respect to the outer section 111, until its tongue 112b snaps its tip 112c against the end of the outer section. Thus, when the user hears two clicks, indicating the snapping of the two tongues 113c and 112b, respectively, into engagement with the ends of the intermediate section 112 and outer section 111, respectively, the user is informed that the telescoping sections 111–113 of the protective enclosure 110 have moved to their extended protective condition, protecting the needle 104 which has been extracted from the cannula 102. When the two tongues have thus snapped into place, they prevent the sections 111–113 from being moved in the opposite direction, towards their nested condition, which would dangerously expose the end of the needle 102.

Figure 14:
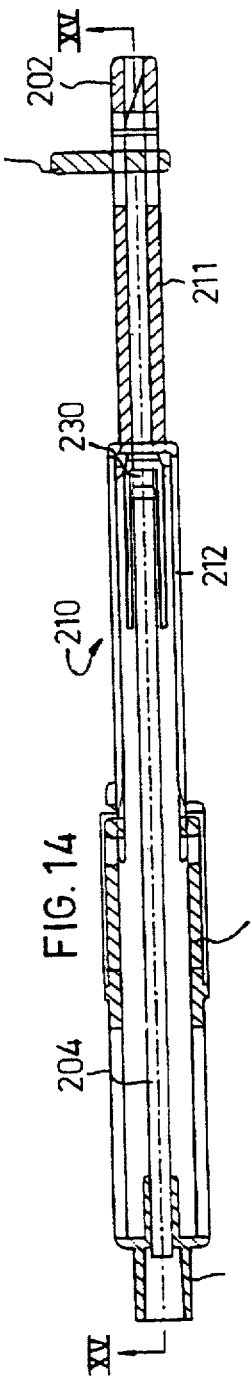
FIGS. 14 and 15 are corresponding views of the cannula assembly of FIGS. 12 and 13, but showing the assembly in the extended protective condition of the enclosure.
Figure 16:
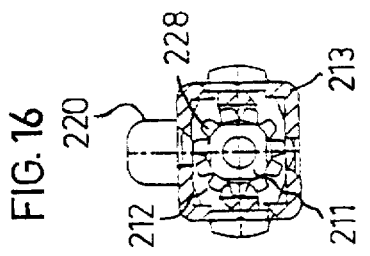
FIG. 16 is an end view of FIG. 14.
Figure 15:
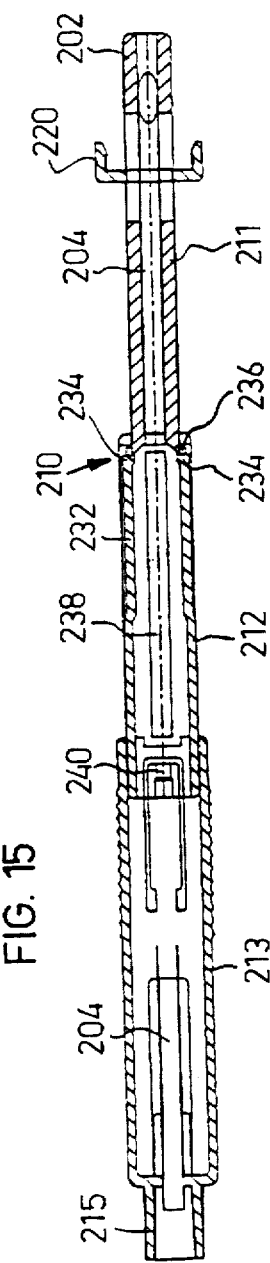

The cannula assembly illustrated in FIGS. 12–23 is similar to those described above, in that it also includes an outer plastic cannula 202, an outer hollow guide needle 204, and a protective enclosure 210 for enclosing the guide needle when moved to its retracted position as illustrated in FIGS. 14 and 15. The protective enclosure 210 also includes three telescopic sections 211, 212, 213, of transverse dimensions increasing from the outer section 211 to the inner section 213, as in the assembly of FIGS. 4–10. The inner section 213 is also formed with a needle hub 215 closed by a hydrophobic plug (not shown) corresponding to plug 16 in FIGS. 1–3. In this case, however, the inner section 213 and intermediate section 212 are of rectangular configuration, as described above, but the outer section 211 is of cylindrical configuration to permit the outer section to rotate with respect to the remaining two sections 212, 213 at all times except when the enclosure is in its fully extended condition. As will be described more particularly below, this arrangement prevents detaching the hub assembly 214 from the Leuer connection 220 carried by the outer section 211 at all times except when the three sections of the enclosure are in their extended protective positions, to assure that the needle is protected against contact when the cannula assembly is removed.

As shown particularly in FIG. 17, the outer section 211 is of hollow cylindrical configuration. At its distal end, it is formed with an annular recess 222 for receiving the Leuer connector 220. For this purpose, the Leuer connector 220 (FIG. 23) is formed with a circular opening 224 substantially equal to, or slightly larger than, the outer diameter of recess 222, but flattened at its opposite ends 224a to decrease the size of that opening along that diameter. In addition, the distal end of the outer section 211 is formed with a pair of axial slots 226 passing through the annular recess 222, to impart radial elasticity to this portion of the outer section 211 in the radial direction. Thus, the Leuer connector 220 may be inserted from the distal end of the outer section 211 and snapped into the annular recess 222 so as to be firmly coupled to the outer section 211 and to rotate with it whenever the outer section rotates with respect to the remaining sections 212 and 213.

The proximal end of the outer section 211 is formed with an annular array of teeth 228 which extend radially outwardly of the remainder of the section. These teeth cooperate with a pair of diametrically-opposed teeth 230 (FIG. 14) in the distal end of the intermediate section 212.

The intermediate section 212 is further formed with a pair of resilient tongues 232 on its opposite sides, each having an inwardly-bent tip 234 terminating short of the respective end of the section to define a gap 236. Resilient tongues 232 permit the intermediate section 212 to be moved outwardly with respect to the outer section 211 until the annular teeth 228 of the outer section reach the distal end of the intermediate section, at which time the end faces of the tongues 232 snap against the end faces of the annular teeth 228 to prevent axial movement of one section with respect to the other in the reverse direction. At this time, teeth 230 of the intermediate section 212 also seat between a pair of the annular teeth 228 in the outer section 211, and thereby also prevent rotary movement of one section with respect to the other.

The outer surface of the intermediate section 212 is further formed with a pair of axially-extending recesses 238, starting from the distal end and terminating short of the proximal end of the section. At its proximal end, the intermediate section 212 is further formed with a pair of square holes 240 in alignment with the recesses 238.

The inner section 213 is similarly formed with a pair of resilient tongues 242, each terminating in an inwardly-bent tip 244. The tips 244 are received within recess 238 of the intermediate section 212 and guide the movement of the inner section with respect to the intermediate section until the two sections are in their fully extended condition, whereupon the tips 244 snap into the openings 240 in the intermediate section. When this occurs, the intermediate section 212 is locked to the inner section 213, with respect to both axial and rotary movements. Since the two telescoping sections 212 and 213 are of rectangular configuration, both sections are locked together during rotation so that they rotate together. However, since the outer section 211 is of cylindrical configuration, it can rotate relative to the intermediate section 212, except when the two sections are in their fully extended condition wherein the teeth 230 on the intermediate section 212 are received between the teeth 228 on the outer section 211.

The cannula assembly illustrated in FIGS. 12–23 is otherwise constructed, and used, substantially in the same manner as described above with respect to the other two assemblies. However, the assembly of FIGS. 12–23 provides better protection against accidental removal of the hub assembly 214 from the Leuer connector 220, except when the three-section enclosure 211, 212, 213 is in its fully extended position to completely enclose the needle 204.

Thus, the cannula hub 214 would normally be detached from the protective enclosure 210 by gripping the inner section 213 of the protective enclosure with one hand, gripping the cannula hub 214 with the other hand, and rotating one with respect to the other in order to detach the cannula hub from the Leuer connector 220 carried by the outer section 211. The tongues 242 of the inner section 213 are of softer resiliency than the tongues 232 of the intermediate section 212, so that when moving the inner section that section will first move outwardly with respect to the intermediate section 212, and then the intermediate section will move with respect to the outer section 211. Until the intermediate section 212 has moved completely with respect to the outer section 211, rotation of the inner section 213 will not rotate the outer section 211 with respect to the Leuer connector 220, so that the cannula hub 214 will remain attached to the Leuer connector carried by the outer section. However, when the intermediate section 212 moves fully with respect to the outer section 211 (which, as described earlier, occurs after the inner section 213 has been moved fully to its outward position), the teeth 230 of the intermediate section seat between the teeth 228 of the outer section, thereby locking the two sections to rotate together, enabling the cannula hub 214 to be detached from the Leuer connector 220.

Once the three sections have been moved to their outermost, extended positions, they cannot thereafter be moved in the opposite direction. This is because the inwardly-bent tips 244 of the resilient tongues 242 in the inner section 213 are received within openings 240 in the intermediate section 212, and the inwardly-bent tips 234 of the resilient tongues 232 in the intermediate section 212 abut against the end of the outer section 211. The snapping of the tips of these two pairs of resilient tongues into their respective locking positions produces two "clicks", which provide a clear indication that the protective enclosure has been moved to its fully extended position for protecting the needle therein before the cannula hub is detached.

It will thus be seen that the use of any one of the cannula assemblies, as described above, does not hamper or substantially change the common practise of using such assemblies. Moreover, the protection of a contaminated needle is automatic and does not necessitate a special needle protection step. Each assembly also prevents re-extension of the needle from the protected configuration. Further, each assembly need not be substantially larger than current products; and finally, each assembly is simple to use and inexpensive to manufacture.

While the invention has been described with respect to two preferred embodiments, it will be appreciated that these are set forth merely for purposes of example, and that many other variations, modifications and applications of the invention may be made.

What is claimed is:

1. An intravenous cannula assembly, comprising:

a cannula having a distal end insertable through an opening in a subject's skin for draining fluid or for introducing a medication via its distal end;

a guide needle in an operative position with respect to said cannula and having a distal end for piercing the subject's skin and for guiding the distal end of the cannula through the subject's skin, said guide needle being movable to a retracted position via the proximal end of the cannula;

and a protective enclosure for enclosing the guide needle when moved to its retracted position;

said protective enclosure comprising a plurality of sections in telescoping relation to each other including an inner section closed at its proximal end by a proximal end wall and open at its distal end, an intermediate section open at both ends, and an outer section open at both ends;

the proximal end of said cannula having a hub secured to the distal end of the outer enclosure section by a quickly-attachable connector;

said proximal end of the guide needle being secured to said proximal end wall of the inner enclosure section such that when the enclosure sections are in a compact nested condition, the guide needle is in its operative position extending through the inner, intermediate and outer enclosure sections and through the cannula, and when the enclosure sections are in an extended protective condition, the guide needle is completely enclosed by the inner, intermediate and outer enclosure sections.

2. The assembly according to claim 1, wherein said quickly-attachable connector includes a pair of diametrically-opposed ribs fixed to the outer section of the protective enclosure and a pair of diametrically-opposed ribs fixed to the cannula hub, one of said pair of ribs being formed with radially-extending projections receivable within recesses formed in said other pair of ribs, such that the protective enclosure, with the guide needle enclosed thereby, may be rotated in either direction to quickly detach it from said cannula.

3. The assembly according to claim 1, wherein said protective enclosure includes blocking means carried by said plurality of sections of the protective enclosure permitting movement of said sections from said compact nested condition to said extended protective condition, but blocking movement of said sections from said extended protective condition to said compact nested condition.

4. The assembly according to claim 3, wherein said blocking means comprises a resilient tongue on at least one of said sections having a free end engageable with an end of the adjacent section in the extended condition of the enclosure.

5. The assembly according to claim 1, wherein the transverse dimensions of said intermediate section of the protective enclosure are larger than those of the outer section but smaller than those of the inner section.

6. The assembly according to claim 1, wherein said intermediate section of the protective enclosure is snapped via an open side over the ends of the outer and outer sections of the protective enclosure to assemble said sections in telescoping relation.

7. The assembly according to claim 2, wherein said pair of ribs fixed to the outer section of the protective enclosure are formed with said radially-extending projections receivable within recesses formed in said pair of ribs fixed to the cannula hub.

8. The assembly according to claim 7, further including rotatable coupling means which couples together the sections of the enclosure for rotation together only in the extended condition of the enclosure.

9. The assembly according to claim 8, wherein said rotatable coupling means includes a tooth at the distal end of said intermediate section cooperable with an annular array of teeth at the proximal end of said outer section.

10. The assembly according to claim 8, wherein said rotatable coupling means includes a tooth at the distal end of said inner section receivable within an opening in the proximal end of the intermediate section.

11. The assembly according to claim 1, wherein said cannula is of plastic material and encloses the guide needle, and wherein said guide needle is hollow and of metal.

* * * * *